United States Patent
Kingsley et al.

(10) Patent No.: US 11,660,109 B2
(45) Date of Patent: May 30, 2023

(54) CUTTING ELEMENTS FOR SURGICAL INSTRUMENTS SUCH AS FOR USE IN ROBOTIC SURGICAL SYSTEMS

(71) Applicant: Covidien LP, Mansfield, MA (US)

(72) Inventors: Dylan R. Kingsley, Broomfield, CO (US); Jason G. Weihe, Longmont, CO (US); William Whitney, Boulder, CO (US); Zachary S. Heiliger, Nederland, CO (US); Curtis M. Siebenaller, Frederick, CO (US); Crystal A. Adams, Westminster, CO (US); David D. Brause, Longmont, CO (US)

(73) Assignee: Covidien LP, Mansfield, MA (US)

( * ) Notice: Subject to any disclaimer, the term of this patent is extended or adjusted under 35 U.S.C. 154(b) by 326 days.

(21) Appl. No.: 17/014,933

(22) Filed: Sep. 8, 2020

(65) Prior Publication Data

US 2022/0071650 A1    Mar. 10, 2022

(51) Int. Cl.
*A61B 17/295* (2006.01)
*A61B 18/14* (2006.01)
*A61B 34/30* (2016.01)

(52) U.S. Cl.
CPC ........ *A61B 17/295* (2013.01); *A61B 18/1445* (2013.01); *A61B 2018/1455* (2013.01); *A61B 2034/301* (2016.02)

(58) Field of Classification Search
CPC .............. A61B 17/295; A61B 17/3209; A61B 17/3211; A61B 2017/07285; A61B 17/068; A61B 2018/1455; A61B 18/1445; A61F 9/0133
See application file for complete search history.

(56) References Cited

U.S. PATENT DOCUMENTS

| | | |
|---|---|---|
| D249,549 S | 9/1978 | Pike |
| 4,161,950 A | 7/1979 | Doss et al. |
| D263,020 S | 2/1982 | Rau, III |
| 4,534,827 A | 8/1985 | Henderson |
| D295,893 S | 5/1988 | Sharkany et al. |
| D295,894 S | 5/1988 | Sharkany et al. |

(Continued)

OTHER PUBLICATIONS

International Search Report and Written Opinion issued in corresponding International Application No. PCT/JS2021/046124 dated Nov. 25, 2021, 12 pages.

*Primary Examiner* — Sarah W Aleman
(74) *Attorney, Agent, or Firm* — Carter, DeLuca & Farrell LLP (57) ABSTRACT

A surgical end effector assembly includes first and second jaw members configured to grasp tissue. At least one of the jaw members defines a channel. A cutting element reciprocates through the channel to cut grasped tissue. The cutting element may include a first bevel defined along a first portion of a distal edge on a first side surface of the cutting element and a second bevel defined along a second portion of the distal edge on a second side surface of the cutting element. The first and second portions of the distal edge are sharpened to facilitate cutting tissue upon distal advancement of the cutting element. Alternatively or additionally, the cutting element may include a proximal body and a distal fin defining a height greater than a height of the proximal body and including a thinned portion defining a depression within a first side surface thereof.

18 Claims, 7 Drawing Sheets

(56) References Cited

U.S. PATENT DOCUMENTS

| | | |
|---|---|---|
| 4,763,669 A | 8/1988 | Jaeger |
| D298,353 S | 11/1988 | Manno |
| D299,413 S | 1/1989 | DeCarolis |
| 5,005,754 A | 4/1991 | Van Overloop |
| 5,100,420 A | 3/1992 | Green et al. |
| 5,258,001 A | 11/1993 | Corman |
| D343,453 S | 1/1994 | Noda |
| 5,304,203 A | 4/1994 | El-Mallawany et al. |
| D348,930 S | 7/1994 | Olson |
| D349,341 S | 8/1994 | Lichtman et al. |
| 5,344,424 A | 9/1994 | Roberts et al. |
| D354,564 S | 1/1995 | Medema |
| D358,887 S | 5/1995 | Feinberg |
| 5,540,685 A | 7/1996 | Parins et al. |
| 5,578,052 A | 11/1996 | Koros et al. |
| 5,611,808 A | 3/1997 | Hossain et al. |
| 5,618,294 A | 4/1997 | Aust et al. |
| D384,413 S | 9/1997 | Zlock et al. |
| 5,665,100 A | 9/1997 | Yoon |
| 5,752,644 A | 5/1998 | Bolanos et al. |
| H1745 H | 8/1998 | Paraschac |
| 5,797,941 A | 8/1998 | Schulze et al. |
| 5,814,043 A | 9/1998 | Shapeton |
| D402,028 S | 12/1998 | Grimm et al. |
| D408,018 S | 4/1999 | McNaughton |
| 5,913,874 A | 6/1999 | Berns et al. |
| 5,960,544 A | 10/1999 | Beyers |
| D416,089 S | 11/1999 | Barton et al. |
| 6,050,996 A | 4/2000 | Schmaltz et al. |
| D424,694 S | 5/2000 | Tetzlaff et al. |
| D425,201 S | 5/2000 | Tetzlaff et al. |
| H1904 H | 10/2000 | Yates et al. |
| 6,293,954 B1 | 9/2001 | Fogarty et al. |
| D449,886 S | 10/2001 | Tetzlaff et al. |
| 6,329,778 B1 | 12/2001 | Culp et al. |
| 6,334,861 B1 | 1/2002 | Chandler et al. |
| D453,923 S | 2/2002 | Olson |
| D454,951 S | 3/2002 | Bon |
| D457,958 S | 5/2002 | Dycus et al. |
| D457,959 S | 5/2002 | Tetzlaff et al. |
| 6,406,485 B1 | 6/2002 | Hossain et al. |
| H2037 H | 7/2002 | Yates et al. |
| 6,464,704 B2 | 10/2002 | Schmaltz et al. |
| D465,281 S | 11/2002 | Lang |
| D466,209 S | 11/2002 | Bon |
| 6,511,480 B1 | 1/2003 | Tetzlaff et al. |
| 6,652,521 B2 | 11/2003 | Schulze |
| 6,673,092 B1 | 1/2004 | Bacher |
| D493,888 S | 8/2004 | Reschke |
| D496,997 S | 10/2004 | Dycus et al. |
| D499,181 S | 11/2004 | Dycus et al. |
| D502,994 S | 3/2005 | Blake, III |
| D509,297 S | 9/2005 | Wells |
| 6,952,086 B1 | 10/2005 | Krefta et al. |
| D525,361 S | 7/2006 | Hushka |
| D531,311 S | 10/2006 | Guerra et al. |
| 7,118,570 B2 | 10/2006 | Tetzlaff et al. |
| D533,274 S | 12/2006 | Visconti et al. |
| D533,942 S | 12/2006 | Kerr et al. |
| D535,027 S | 1/2007 | James et al. |
| D538,932 S | 3/2007 | Malik |
| D541,418 S | 4/2007 | Schechter et al. |
| D541,611 S | 5/2007 | Aglassinger |
| D541,938 S | 5/2007 | Kerr et al. |
| D545,432 S | 6/2007 | Watanabe |
| D547,154 S | 7/2007 | Lee |
| 7,329,257 B2 | 2/2008 | Kanehira et al. |
| D564,662 S | 3/2008 | Moses et al. |
| D567,943 S | 4/2008 | Moses et al. |
| D575,395 S | 8/2008 | Hushka |
| D575,401 S | 8/2008 | Hixson et al. |
| 7,431,730 B2 | 10/2008 | Viola |
| D582,038 S | 12/2008 | Swoyer et al. |
| 7,540,872 B2 | 6/2009 | Schechter et al. |
| 7,641,653 B2 | 1/2010 | Dalla Betta et al. |
| D617,900 S | 6/2010 | Kingsley et al. |
| D617,901 S | 6/2010 | Unger et al. |
| D617,902 S | 6/2010 | Twomey et al. |
| D617,903 S | 6/2010 | Unger et al. |
| D618,798 S | 6/2010 | Olson et al. |
| 7,744,615 B2 | 6/2010 | Couture |
| D621,503 S | 8/2010 | Otten et al. |
| 7,766,928 B2 | 8/2010 | Ezzat et al. |
| 7,799,039 B2 | 9/2010 | Shelton, IV et al. |
| D627,462 S | 11/2010 | Kingsley |
| D628,289 S | 11/2010 | Romero |
| D628,290 S | 11/2010 | Romero |
| 7,854,185 B2 | 12/2010 | Zhang et al. |
| D630,324 S | 1/2011 | Reschke |
| 7,896,878 B2 | 3/2011 | Johnson et al. |
| 7,955,332 B2 | 6/2011 | Arts et al. |
| D649,249 S | 11/2011 | Guerra |
| D649,643 S | 11/2011 | Allen, IV et al. |
| 8,147,489 B2 | 4/2012 | Moses et al. |
| D661,394 S | 6/2012 | Romero et al. |
| 8,241,282 B2 | 8/2012 | Unger et al. |
| 8,287,536 B2 | 10/2012 | Mueller et al. |
| 8,298,233 B2 | 10/2012 | Mueller |
| D670,808 S | 11/2012 | Moua et al. |
| 8,366,709 B2 | 2/2013 | Schechter et al. |
| 8,394,096 B2 | 3/2013 | Moses et al. |
| D680,220 S | 4/2013 | Rachlin |
| 8,409,246 B2 | 4/2013 | Kerr et al. |
| 8,409,247 B2 | 4/2013 | Garrison et al. |
| 8,425,504 B2 | 4/2013 | Orton et al. |
| 8,425,511 B2 | 4/2013 | Olson |
| 8,430,877 B2 | 4/2013 | Kerr et al. |
| 8,439,913 B2 | 5/2013 | Horner et al. |
| 8,469,716 B2 | 6/2013 | Fedotov et al. |
| 8,469,991 B2 | 6/2013 | Kerr |
| 8,469,992 B2 | 6/2013 | Roy et al. |
| 8,480,671 B2 | 7/2013 | Mueller |
| 8,491,624 B2 | 7/2013 | Kerr et al. |
| 8,491,625 B2 | 7/2013 | Horner |
| 8,491,626 B2 | 7/2013 | Roy et al. |
| 8,512,336 B2 | 8/2013 | Couture |
| 8,540,749 B2 | 9/2013 | Garrison et al. |
| 8,551,091 B2 | 10/2013 | Couture et al. |
| 8,556,929 B2 | 10/2013 | Harper et al. |
| 8,568,397 B2 | 10/2013 | Horner et al. |
| 8,568,408 B2 | 10/2013 | Townsend et al. |
| 8,585,736 B2 | 11/2013 | Horner et al. |
| 8,591,510 B2 | 11/2013 | Allen, IV et al. |
| 8,597,295 B2 | 12/2013 | Kerr |
| 8,623,018 B2 | 1/2014 | Horner et al. |
| 8,628,557 B2 | 1/2014 | Collings et al. |
| 8,641,712 B2 | 2/2014 | Couture |
| 8,647,343 B2 | 2/2014 | Chojin et al. |
| 8,652,135 B2 | 2/2014 | Nau, Jr. |
| 8,663,222 B2 | 3/2014 | Anderson et al. |
| 8,672,939 B2 | 3/2014 | Garrison |
| 8,679,098 B2 | 3/2014 | Hart |
| 8,685,009 B2 | 4/2014 | Chernov et al. |
| 8,685,021 B2 | 4/2014 | Chernov et al. |
| 8,685,056 B2 | 4/2014 | Evans et al. |
| 8,702,737 B2 | 4/2014 | Chojin et al. |
| 8,702,749 B2 | 4/2014 | Twomey |
| 8,734,445 B2 | 5/2014 | Johnson et al. |
| 8,740,898 B2 | 6/2014 | Chojin et al. |
| 8,745,840 B2 | 6/2014 | Hempstead et al. |
| 8,747,434 B2 | 6/2014 | Larson et al. |
| 8,756,785 B2 | 6/2014 | Allen, IV et al. |
| 8,784,418 B2 | 7/2014 | Romero |
| 8,795,269 B2 | 8/2014 | Garrison |
| 8,808,288 B2 | 8/2014 | Reschke |
| 8,814,864 B2 | 8/2014 | Gilbert |
| 8,840,639 B2 | 9/2014 | Gerhardt, Jr. et al. |
| 8,845,636 B2 | 9/2014 | Allen, IV et al. |
| 8,852,185 B2 | 10/2014 | Twomey |
| 8,852,228 B2 | 10/2014 | Nau, Jr. |
| 8,858,547 B2 | 10/2014 | Brogna |
| 8,858,553 B2 | 10/2014 | Chojin |
| 8,864,753 B2 | 10/2014 | Nau, Jr. et al. |
| 8,864,795 B2 | 10/2014 | Kerr et al. |

(56) References Cited

U.S. PATENT DOCUMENTS

| | | |
|---|---|---|
| 8,887,373 B2 | 11/2014 | Brandt et al. |
| 8,888,771 B2 | 11/2014 | Twomey |
| 8,888,775 B2 | 11/2014 | Nau, Jr. et al. |
| 8,898,888 B2 | 12/2014 | Brandt et al. |
| 8,900,232 B2 | 12/2014 | Ourada |
| 8,906,018 B2 | 12/2014 | Rooks et al. |
| 8,920,421 B2 | 12/2014 | Rupp |
| 8,932,293 B2 | 1/2015 | Chernov et al. |
| 8,936,614 B2 | 1/2015 | Allen, IV |
| 8,939,972 B2 | 1/2015 | Twomey |
| 8,945,175 B2 | 2/2015 | Twomey |
| 8,961,504 B2 | 2/2015 | Hoarau et al. |
| 8,961,514 B2 | 2/2015 | Garrison |
| 8,968,283 B2 | 3/2015 | Kharin |
| 8,968,305 B2 | 3/2015 | Dumbauld et al. |
| 8,968,309 B2 | 3/2015 | Roy et al. |
| 8,968,316 B2 | 3/2015 | Roy et al. |
| 8,968,357 B2 | 3/2015 | Mueller |
| 8,968,359 B2 | 3/2015 | Kerr et al. |
| 9,005,200 B2 | 4/2015 | Roy et al. |
| 9,017,372 B2 | 4/2015 | Artale et al. |
| 9,028,484 B2 | 5/2015 | Craig |
| 9,028,492 B2 | 5/2015 | Kerr et al. |
| 9,028,495 B2 | 5/2015 | Mueller et al. |
| 9,039,704 B2 | 5/2015 | Joseph |
| 9,039,732 B2 | 5/2015 | Sims et al. |
| 9,055,961 B2 | 6/2015 | Manzo et al. |
| 9,084,608 B2 | 7/2015 | Larson et al. |
| 9,113,933 B2 | 8/2015 | Chernova et al. |
| 9,113,934 B2 | 8/2015 | Chernov et al. |
| 9,161,807 B2 | 10/2015 | Garrison |
| 9,211,657 B2 | 12/2015 | Ackley et al. |
| 9,265,568 B2 | 2/2016 | Chernov et al. |
| 9,333,002 B2 | 5/2016 | Garrison |
| 9,381,059 B2 | 7/2016 | Garrison |
| 9,456,870 B2 | 10/2016 | Chernov et al. |
| 9,498,278 B2 | 11/2016 | Couture et al. |
| 9,498,279 B2 | 11/2016 | Artale et al. |
| 9,504,519 B2 | 11/2016 | Kerr et al. |
| 9,585,709 B2 | 3/2017 | Krapohl |
| 9,615,877 B2 | 4/2017 | Tyrrell et al. |
| 9,655,672 B2 | 5/2017 | Artale et al. |
| 2003/0018332 A1 | 1/2003 | Schmaltz et al. |
| 2003/0109875 A1 | 6/2003 | Tetzlaff et al. |
| 2003/0111507 A1 | 6/2003 | Nunez |
| 2003/0199869 A1 | 10/2003 | Johnson et al. |
| 2003/0220637 A1 | 11/2003 | Truckai et al. |
| 2003/0229344 A1 | 12/2003 | Dycus et al. |
| 2004/0092927 A1 | 5/2004 | Podhajsky et al. |
| 2005/0070889 A1 | 3/2005 | Nobis et al. |
| 2005/0107784 A1 | 5/2005 | Moses et al. |
| 2005/0113826 A1 | 5/2005 | Johnson et al. |
| 2005/0113828 A1 | 5/2005 | Shields et al. |
| 2005/0159745 A1 | 7/2005 | Truckai et al. |
| 2006/0253126 A1 | 11/2006 | Bjerken et al. |
| 2007/0062017 A1 | 3/2007 | Dycus et al. |
| 2007/0088356 A1 | 4/2007 | Moses et al. |
| 2007/0179499 A1 | 8/2007 | Garrison |
| 2007/0260241 A1 | 11/2007 | Dalla Betta et al. |
| 2008/0215048 A1 | 9/2008 | Hafner et al. |
| 2009/0131934 A1 | 5/2009 | Odom et al. |
| 2009/0171353 A1 | 7/2009 | Johnson et al. |
| 2009/0182327 A1 | 7/2009 | Unger |
| 2009/0240246 A1 | 9/2009 | Deville et al. |
| 2009/0302090 A1 | 12/2009 | Shah |
| 2009/0308909 A1 | 12/2009 | Nalagatla et al. |
| 2010/0016857 A1 | 1/2010 | McKenna et al. |
| 2010/0130977 A1 | 5/2010 | Garrison et al. |
| 2010/0179545 A1 | 7/2010 | Twomey et al. |
| 2010/0179547 A1 | 7/2010 | Cunningham et al. |
| 2010/0193568 A1 | 8/2010 | Scheib et al. |
| 2010/0228250 A1 | 9/2010 | Brogna |
| 2010/0274244 A1 | 10/2010 | Heard |
| 2010/0292691 A1 | 11/2010 | Brogna |
| 2010/0305567 A1 | 12/2010 | Swanson |
| 2011/0054469 A1 | 3/2011 | Kappus et al. |
| 2011/0060314 A1 | 3/2011 | Wallace et al. |
| 2011/0060356 A1 | 3/2011 | Reschke et al. |
| 2011/0072638 A1 | 3/2011 | Brandt et al. |
| 2011/0087218 A1 | 4/2011 | Boudreaux et al. |
| 2011/0218530 A1 | 9/2011 | Reschke |
| 2011/0238065 A1 | 9/2011 | Hunt et al. |
| 2011/0238067 A1 | 9/2011 | Moses et al. |
| 2011/0257680 A1 | 10/2011 | Reschke et al. |
| 2011/0270245 A1 | 11/2011 | Horner et al. |
| 2011/0270251 A1 | 11/2011 | Horner et al. |
| 2011/0276049 A1 | 11/2011 | Gerhardt |
| 2011/0295313 A1 | 12/2011 | Kerr |
| 2012/0059372 A1 | 3/2012 | Johnson |
| 2012/0059409 A1 | 3/2012 | Reschke et al. |
| 2012/0083785 A1 | 4/2012 | Roy et al. |
| 2012/0083786 A1 | 4/2012 | Artale et al. |
| 2012/0083827 A1 | 4/2012 | Artale et al. |
| 2012/0123402 A1 | 5/2012 | Chernov et al. |
| 2012/0123404 A1 | 5/2012 | Craig |
| 2012/0123410 A1 | 5/2012 | Craig |
| 2012/0130367 A1 | 5/2012 | Garrison |
| 2012/0136354 A1 | 5/2012 | Rupp |
| 2012/0172868 A1 | 7/2012 | Twomey et al. |
| 2012/0172873 A1 | 7/2012 | Artale et al. |
| 2012/0172924 A1 | 7/2012 | Allen, IV |
| 2012/0184988 A1 | 7/2012 | Twomey et al. |
| 2012/0184989 A1 | 7/2012 | Twomey |
| 2012/0184990 A1 | 7/2012 | Twomey |
| 2012/0191120 A1 | 7/2012 | Linsi |
| 2012/0209263 A1 | 8/2012 | Sharp et al. |
| 2012/0215219 A1 | 8/2012 | Roy et al. |
| 2012/0239034 A1 | 9/2012 | Horner et al. |
| 2012/0253344 A1 | 10/2012 | Dumbauld et al. |
| 2012/0259331 A1 | 10/2012 | Garrison |
| 2012/0265241 A1 | 10/2012 | Hart et al. |
| 2012/0283727 A1 | 11/2012 | Twomey |
| 2012/0296205 A1 | 11/2012 | Chernov et al. |
| 2012/0296238 A1 | 11/2012 | Chernov et al. |
| 2012/0296239 A1 | 11/2012 | Chernov et al. |
| 2012/0296317 A1 | 11/2012 | Chernov et al. |
| 2012/0296323 A1 | 11/2012 | Chernov et al. |
| 2012/0296324 A1 | 11/2012 | Chernov et al. |
| 2012/0296334 A1 | 11/2012 | Kharin |
| 2012/0303025 A1 | 11/2012 | Garrison |
| 2012/0323238 A1 | 12/2012 | Tyrrell et al. |
| 2012/0330308 A1 | 12/2012 | Joseph |
| 2012/0330309 A1 | 12/2012 | Joseph |
| 2013/0018364 A1 | 1/2013 | Chernov et al. |
| 2013/0018372 A1 | 1/2013 | Sims et al. |
| 2013/0018411 A1 | 1/2013 | Collings et al. |
| 2013/0022495 A1 | 1/2013 | Allen, IV et al. |
| 2013/0030432 A1 | 1/2013 | Garrison et al. |
| 2013/0041370 A1 | 2/2013 | Unger |
| 2013/0046295 A1 | 2/2013 | Kerr et al. |
| 2013/0046303 A1 | 2/2013 | Evans et al. |
| 2013/0046306 A1 | 2/2013 | Evans et al. |
| 2013/0046337 A1 | 2/2013 | Evans et al. |
| 2013/0060250 A1 | 3/2013 | Twomey et al. |
| 2013/0066318 A1 | 3/2013 | Kerr |
| 2013/0071282 A1 | 3/2013 | Fry |
| 2013/0072927 A1 | 3/2013 | Allen, IV et al. |
| 2013/0079760 A1 | 3/2013 | Twomey et al. |
| 2013/0079762 A1 | 3/2013 | Twomey et al. |
| 2013/0079774 A1 | 3/2013 | Whitney et al. |
| 2013/0085491 A1 | 4/2013 | Twomey et al. |
| 2013/0085496 A1 | 4/2013 | Unger et al. |
| 2013/0103030 A1 | 4/2013 | Garrison |
| 2013/0103031 A1 | 4/2013 | Garrison |
| 2013/0103035 A1 | 4/2013 | Horner et al. |
| 2013/0123837 A1 | 5/2013 | Roy et al. |
| 2013/0138101 A1 | 5/2013 | Kerr |
| 2013/0138102 A1 | 5/2013 | Twomey et al. |
| 2013/0138129 A1 | 5/2013 | Garrison et al. |
| 2013/0144284 A1 | 6/2013 | Behnke, II et al. |
| 2013/0178852 A1 | 7/2013 | Allen, IV et al. |
| 2013/0185922 A1 | 7/2013 | Twomey et al. |
| 2013/0190753 A1 | 7/2013 | Garrison et al. |
| 2013/0190760 A1 | 7/2013 | Allen, IV et al. |

(56) References Cited

U.S. PATENT DOCUMENTS

| | | |
|---|---|---|
| 2013/0197503 A1 | 8/2013 | Orszulak |
| 2013/0226177 A1 | 8/2013 | Brandt et al. |
| 2014/0155878 A1 | 6/2014 | Trees et al. |
| 2014/0221994 A1 | 8/2014 | Reschke |
| 2014/0221995 A1 | 8/2014 | Guerra et al. |
| 2014/0221999 A1 | 8/2014 | Cunningham et al. |
| 2014/0228842 A1 | 8/2014 | Dycus et al. |
| 2014/0230243 A1 | 8/2014 | Roy et al. |
| 2014/0236149 A1 | 8/2014 | Kharin et al. |
| 2014/0243811 A1 | 8/2014 | Reschke et al. |
| 2014/0243824 A1 | 8/2014 | Gilbert |
| 2014/0249528 A1 | 9/2014 | Hixson et al. |
| 2014/0250686 A1 | 9/2014 | Hempstead et al. |
| 2014/0257274 A1* | 9/2014 | McCullough, Jr. ............ A61B 18/1445 606/42 |
| 2014/0257283 A1 | 9/2014 | Johnson et al. |
| 2014/0257284 A1 | 9/2014 | Artale |
| 2014/0257285 A1 | 9/2014 | Moua |
| 2014/0276803 A1 | 9/2014 | Hart |
| 2014/0284313 A1 | 9/2014 | Allen, IV et al. |
| 2014/0288549 A1 | 9/2014 | McKenna et al. |
| 2014/0288553 A1 | 9/2014 | Johnson et al. |
| 2014/0330308 A1 | 11/2014 | Hart et al. |
| 2014/0336635 A1 | 11/2014 | Hart et al. |
| 2014/0353188 A1 | 12/2014 | Reschke et al. |
| 2015/0018816 A1 | 1/2015 | Latimer |
| 2015/0025528 A1 | 1/2015 | Arts |
| 2015/0032106 A1 | 1/2015 | Rachlin |
| 2015/0051598 A1 | 2/2015 | Orszulak et al. |
| 2015/0051640 A1 | 2/2015 | Twomey et al. |
| 2015/0066026 A1 | 3/2015 | Hart et al. |
| 2015/0066076 A1 | 3/2015 | Kerr et al. |
| 2015/0080889 A1 | 3/2015 | Cunningham et al. |
| 2015/0082928 A1 | 3/2015 | Kappus et al. |
| 2015/0083782 A1 | 3/2015 | Scheib et al. |
| 2015/0088122 A1 | 3/2015 | Jensen |
| 2015/0088126 A1 | 3/2015 | Duffin et al. |
| 2015/0088128 A1 | 3/2015 | Couture |
| 2015/0094714 A1 | 4/2015 | Lee et al. |
| 2015/0209067 A1* | 7/2015 | Stamm ............ A61B 17/3209 606/174 |
| 2016/0157925 A1 | 6/2016 | Artale et al. |
| 2016/0175031 A1 | 6/2016 | Boudreaux |
| 2017/0128120 A1 | 5/2017 | Cho et al. |
| 2017/0319230 A1* | 11/2017 | Kunimune ......... A61B 17/3211 |
| 2018/0325582 A1 | 11/2018 | Goodman et al. |
| 2019/0216561 A1 | 7/2019 | Manzo et al. |
| 2020/0237455 A1 | 7/2020 | Anglese |

\* cited by examiner

CUTTING ELEMENTS FOR SURGICAL INSTRUMENTS SUCH AS FOR USE IN ROBOTIC SURGICAL SYSTEMS

FIELD

The present disclosure relates to surgical instruments and, more specifically, to cutting elements for surgical instruments such as for use in robotic surgical systems.

BACKGROUND

Robotic surgical systems are increasingly utilized in various different surgical procedures. Some robotic surgical systems include a console supporting a robotic arm. One or more different surgical instruments may be configured for use with the robotic surgical system and selectively mountable to the robotic arm. The robotic arm provides one or more inputs to the mounted surgical instrument to enable operation of the mounted surgical instrument.

A surgical forceps, one type of instrument capable of being utilized with a robotic surgical system, relies on mechanical action between its jaw members to grasp, clamp, and constrict tissue. Electrosurgical forceps utilize both mechanical clamping action and energy to heat tissue to treat, e.g., coagulate, cauterize, or seal, tissue. Typically, once tissue is treated, the tissue is severed using a cutting element. Accordingly, electrosurgical forceps are designed to incorporate a cutting element to effectively sever treated tissue.

SUMMARY

As used herein, the term "distal" refers to the portion that is being described which is further from an operator (whether a human surgeon or a surgical robot), while the term "proximal" refers to the portion that is being described which is closer to the operator. The terms "about," "substantially," and the like, as utilized herein, are meant to account for manufacturing, material, environmental, use, and/or measurement tolerances and variations, and in any event may encompass differences of up to 10%. Further, to the extent consistent, any of the aspects described herein may be used in conjunction with any or all of the other aspects described herein.

Provided in accordance with aspects of the present disclosure is an end effector assembly of a surgical instrument including first and second jaw members at least one of which is movable relative to the other between a spaced-apart position and an approximated position to grasp tissue between opposing tissue-contacting surfaces thereof. At least one of the first or second jaw members defines a channel. A cutting element is configured to reciprocate through the channel and between the first and second jaw members to cut tissue grasped between the opposing tissue-contacting surfaces. The cutting element includes first and second side surfaces and a distal edge. A first bevel is defined along a first portion of the distal edge on the first side surface and a second bevel is defined along a second portion of the distal edge on the second side surface. The first and second bevels are configured such that the first and second portions of the distal edge are sharpened to facilitate cutting tissue upon distal advancement of the cutting element between the first and second jaw members.

In an aspect of the present disclosure, the cutting element includes a proximal body and a distal fin. The distal fin is defined by the distal edge, an upper edge extending from the distal edge, and a proximal edge extending from the upper edge. In such aspects, the second bevel may extend to or along at least a portion of the upper edge.

In another aspect of the present disclosure, a transition is defined on the distal edge between the first bevel and the second bevel. The transition may be one of: an overlapping portion of the first and second bevels; a gap between the first and second bevels; or a line defining an end of one of the first or second bevels and a beginning of the other of the first or second bevels.

In yet another aspect of the present disclosure, the transition is exposed between the first and second jaw members upon reciprocation of the cutting element therethrough.

In still another aspect of the present disclosure, at least a portion of each of the first and second bevels is exposed between the first and second jaw members upon reciprocation of the cutting element therethrough.

In still yet another aspect of the present disclosure, a cutting actuation rod is attached to the cutting element and configured to reciprocate the cutting element between the first and second jaw members. In such aspects, the cutting actuation rod may be configured to extend through a cut-out defined within one of the first or second jaw members and disposed in communication with the channel.

Another end effector assembly of a surgical instrument provided in accordance with the present disclosure includes first and second jaw members at least one of which is movable relative to the other between a spaced-apart position and an approximated position to grasp tissue between opposing tissue-contacting surfaces thereof. At least one of the first or second jaw members defines a channel. A cutting element is configured to reciprocate through the channel and between the first and second jaw members to cut tissue grasped between the opposing tissue-contacting surfaces. The cutting element includes a proximal body and a distal fin defining a height greater than a height of the proximal body. The distal fin has first and second side surfaces and is defined by a distal edge, an upper edge extending from the distal edge, and a proximal edge extending from the upper edge. The distal fin includes a thinned portion defining a depression within the first side surface thereof.

In an aspect of the present disclosure, at least a portion of the distal edge is sharpened to facilitate cutting tissue upon distal advancement of the cutting element between the first and second jaw members.

In another aspect of the present disclosure, the thinned portion is defined within a section of the distal fin that extends upwardly beyond the height of the proximal body. Additionally or alternatively, the thinned portion extends across the distal fin from the distal edge to the proximal edge.

In still another aspect of the present disclosure, a cutting actuation rod is attached to the proximal body of the cutting element and configured to reciprocate the cutting element between the first and second jaw members. In such aspects, the cutting actuation rod may be configured to extend through a cut-out defined within one of the first or second jaw members and disposed in communication with the channel.

In yet another aspect of the present disclosure, the channel is curved such that the cutting element defines a curved cutting path when reciprocated through the at least one channel. In such aspects, the depression defined within the first side surface of the cutting element may be disposed on a convex side of the curved cutting path.

In still yet another aspect of the present disclosure, the first and second jaw members are curved and the channel is curved similarly as the first and second jaw members.

BRIEF DESCRIPTION OF THE DRAWINGS

Various aspects and features of the present disclosure are described hereinbelow with reference to the drawings wherein.

DETAILED DESCRIPTION

Figure 1:
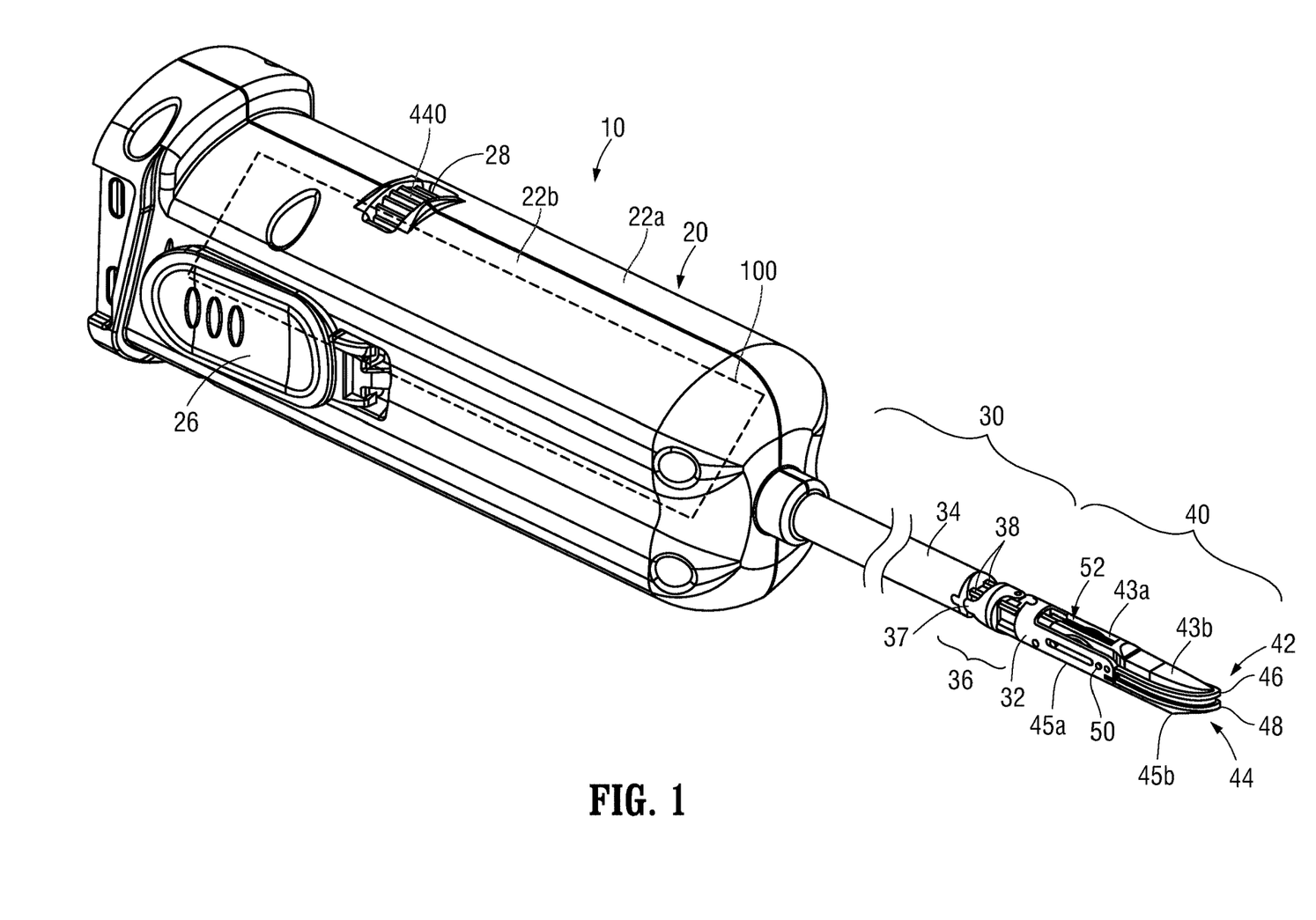
FIG. 1 is a perspective view of a surgical instrument in accordance with the present disclosure configured for mounting on a robotic arm of a robotic surgical system.
Figure 2:
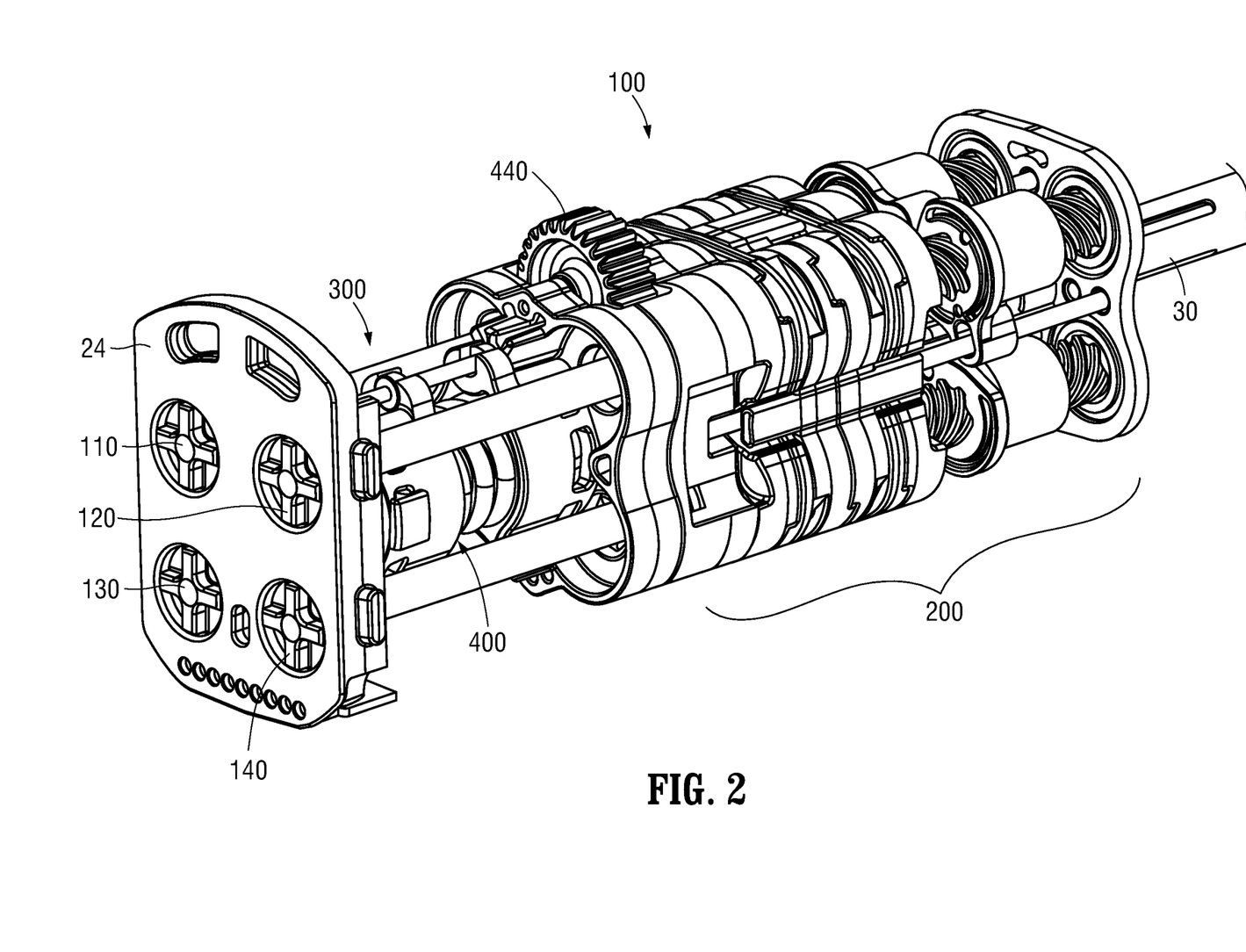
FIG. 2 is a rear perspective view of a proximal portion of the surgical instrument of FIG. 1 with an outer housing removed.
Figure 3:
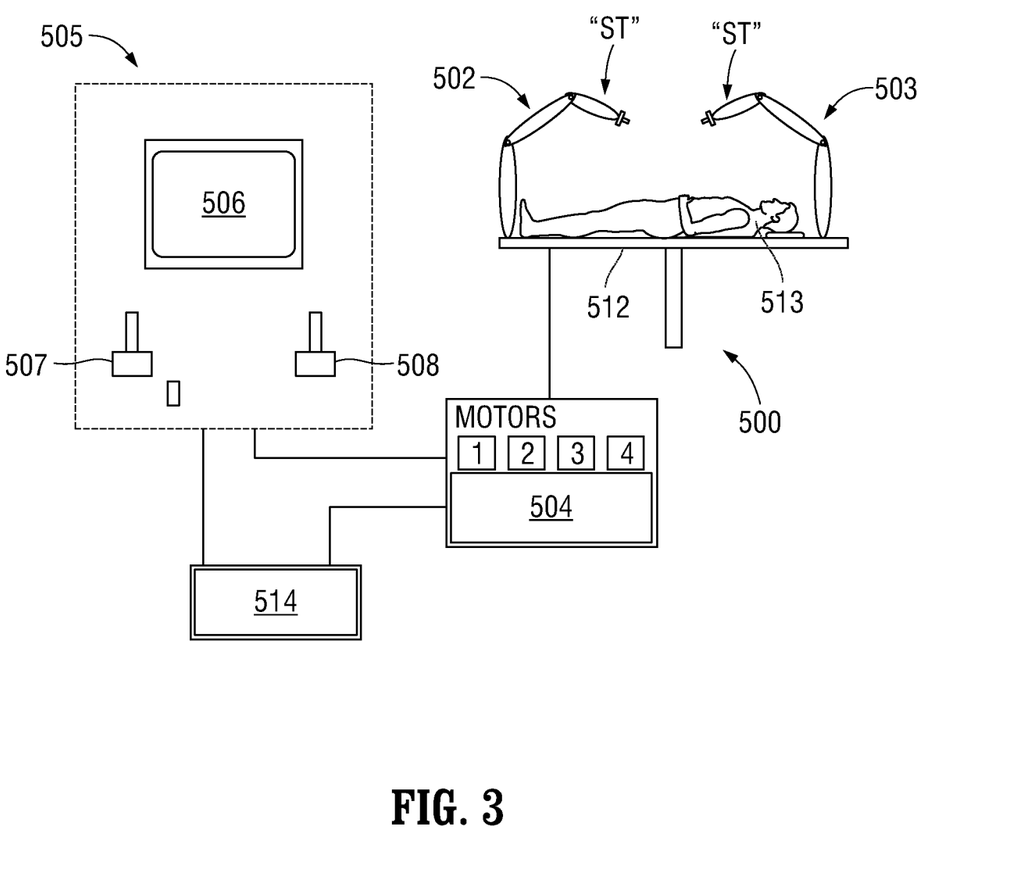
FIG. 3 is a schematic illustration of an exemplary robotic surgical system configured to releasably receive the surgical instrument of FIG. 1.

Referring to FIGS. 1 and 2, a surgical instrument 10 provided in accordance with the present disclosure generally includes a housing 20, a shaft 30 extending distally from housing 20, an end effector assembly 40 extending distally from shaft 30, and an actuation assembly 100 disposed within housing 20 and operably associated with shaft 30 and end effector assembly 40. Instrument 10 is detailed herein as an articulating electrosurgical forceps configured for use with a robotic surgical system, e.g., robotic surgical system 500 (FIG. 3). However, the aspects and features of instrument 10 provided in accordance with the present disclosure, detailed below, are equally applicable for use with other suitable surgical instruments (including non-robotic surgical instrument) and/or in other suitable surgical systems (including non-robotic surgical systems).

Housing 20 of instrument 10 includes first and second body portion 22a, 22b and a proximal face plate 24 (FIG. 2) that cooperate to enclose actuation assembly 100 therein. Proximal face plate 24 includes apertures defined therein through which inputs 110-140 of actuation assembly 100 extend. A pair of latch levers 26 (only one of which is illustrated in FIG. 1) extends outwardly from opposing sides of housing 20 and enables releasable engagement (directly or indirectly) of housing 20 with a robotic arm of a surgical system, e.g., robotic surgical system 500 (FIG. 3). An aperture 28 defined through housing 20 permits thumbwheel 440 to extend therethrough to enable manual manipulation of thumbwheel 440 from the exterior of housing 20 to permit manual opening and closing of end effector assembly 40.

Shaft 30 of instrument 10 includes a distal segment 32, a proximal segment 34, and an articulating section 36 disposed between the distal and proximal segments 32, 34, respectively. Articulating section 36 includes one or more articulating components 37, e.g., links, joints, etc. A plurality of articulation cables 38, e.g., four (4) articulation cables, or other suitable actuators, extends through articulating section 36. More specifically, articulation cables 38 are operably coupled to distal segment 32 of shaft 30 at the distal ends thereof and extend proximally from distal segment 32 of shaft 30, through articulating section 36 of shaft 30 and proximal segment 34 of shaft 30, and into housing 20, wherein articulation cables 38 operably couple with an articulation assembly 200 of actuation assembly 100 to enable selective articulation of distal segment 32 (and, thus end effector assembly 40) relative to proximal segment 34 and housing 20, e.g., about at least two axes of articulation (yaw and pitch articulation, for example). Articulation cables 38 are arranged in a generally rectangular configuration, although other suitable configurations are also contemplated.

With respect to articulation of end effector assembly 40 relative to proximal segment 34 of shaft 30, actuation of articulation cables 38 is effected in pairs. More specifically, in order to pitch end effector assembly 40, the upper pair of cables 38 is actuated in a similar manner while the lower pair of cables 38 is actuated in a similar manner relative to one another but an opposite manner relative to the upper pair of cables 38. With respect to yaw articulation, the right pair of cables 38 is actuated in a similar manner while the left pair of cables 38 is actuated in a similar manner relative to one another but an opposite manner relative to the right pair of cables 38.

End effector assembly 40 includes first and second jaw members 42, 44, respectively. Each jaw member 42, 44 includes a proximal flange portion 43a, 45a and a distal body portion 43b, 45b, respectively. Distal body portions 43b, 45b define opposed tissue-contacting surfaces 46, 48, respectively. Proximal flange portions 43a, 45a are pivotably coupled to one another about a pivot 50 and are operably coupled to one another via a cam-slot assembly 52 including a cam pin slidably received within cam slots defined within the proximal flange portion 43a, 45a of at least one of the jaw members 42, 44, respectively, to enable pivoting of jaw member 42 relative to jaw member 44 and distal segment 32 of shaft 30 between a spaced-apart position (e.g., an open position of end effector assembly 40) and an approximated position (e.g. a closed position of end effector assembly 40) for grasping tissue between tissue-contacting surfaces 46, 48. As an alternative to this unilateral configuration, a bilateral configuration may be provided whereby both jaw members 42, 44 are pivotable relative to one another and distal segment 32 of shaft 30.

Longitudinally-extending channels, e.g., channel 47 of jaw member 44 (FIGS. 4 and 5) and/or a corresponding channel (not shown) of jaw member 42, are defined through tissue-contacting surfaces 46, 48, respectively, of jaw members 42, 44. A cutting assembly 70 (FIG. 6) is provided including a selectively advancable cutting element 72 that enables cutting of tissue grasped between tissue-contacting surfaces 46, 48 of jaw members 42, 44, respectively. A cutting drive assembly 300 (FIG. 2) of actuation assembly 100 provides for selective actuation of cutting assembly 70 to reciprocate the cutting element 72 through jaw members 42, 44 to cut tissue grasped between tissue-contacting surfaces 46, 48. Cutting drive assembly 300 (FIG. 2) is operably coupled between a cutting actuation rod 74 of cutting assembly 70 (FIGS. 4 and 6) and third input 130 of actuation assembly 100 such that, upon receipt of appropriate rotational input into third input 130, cutting drive assembly 300 manipulates cutting actuation rod 74 to reciprocate cutting element 72 between jaw members 42, 44 to cut tissue grasped between tissue-contacting surfaces 46, 48.

Continuing with reference to FIGS. 1 and 2, a drive rod (not shown) is operably coupled to cam-slot assembly 52 of end effector assembly 40, e.g., engaged with the cam pin thereof, such that longitudinal actuation of the drive rod pivots jaw member 42 relative to jaw member 44 between the spaced-apart and approximated positions. More specifically, urging the drive rod proximally pivots jaw member 42 relative to jaw member 44 towards the approximated position while urging the drive rod distally pivots jaw member 42 relative to jaw member 44 towards the spaced-apart position. However, other suitable mechanisms and/or configurations for pivoting jaw member 42 relative to jaw member 44 between the spaced-apart and approximated positions in response to selective actuation of a drive rod are also contemplated. The drive rod extends proximally from end effector assembly 40 through shaft 30 and into housing 20 wherein the drive rod is operably coupled with a jaw drive assembly 400 of actuation assembly 100 (FIG. 2) to enable selective actuation of end effector assembly 40 to grasp tissue therebetween and apply a closure force within an appropriate jaw closure force range.

Tissue-contacting surfaces 46, 48 of jaw members 42, 44, respectively, are at least partially formed from an electrically conductive material and are energizable to different potentials to enable the conduction of electrical energy through tissue grasped therebetween, although tissue-contacting surfaces 46, 48 may alternatively be configured to supply any suitable energy, e.g., thermal, microwave, light, ultrasonic, etc., through tissue grasped therebetween for energy-based tissue treatment. Instrument 10 defines a conductive pathway (not shown) through housing 20 and shaft 30 to end effector assembly 40 that may include lead wires, contacts, and/or electrically-conductive components to enable electrical connection of tissue-contacting surfaces 46, 48 of jaw members 42, 44, respectively, to an energy source (not shown), e.g., an electrosurgical generator via an electrosurgical cable extending therebetween, for supplying energy to tissue-contacting surfaces 46, 48 to treat, e.g., seal, tissue grasped between tissue-contacting surfaces 46, 48.

As noted above, actuation assembly 100 is disposed within housing 20 and includes an articulation assembly 200, cutting drive assembly 300, and jaw drive assembly 400. Articulation assembly 200 is operably coupled between first and second inputs 110, 120, respectively, of actuation assembly 100 and articulation cables 38 (FIG. 1) such that, upon receipt of appropriate rotational inputs into first and/or second inputs 110, 120, articulation assembly 200 manipulates cables 38 (FIG. 1) to articulate end effector assembly 40 in a desired direction, e.g., to pitch and/or yaw end effector assembly 40. Cutting drive assembly 300, s noted above, enables reciprocation of cutting element 72 between jaw members 42, 44 to cut tissue grasped between tissue-contacting surfaces 46, 48 in response to receipt of appropriate rotational input into third input 130. Jaw drive assembly 400 is operably coupled between fourth input 140 of actuation assembly 100 and the drive rod such that, upon receipt of appropriate rotational input into fourth input 140, jaw drive assembly 400 pivots jaw members 42, 44 between the spaced-apart and approximated positions to grasp tissue therebetween and apply a closure force within an appropriate closure force range.

Actuation assembly 100 is configured to operably interface with a robotic surgical system 500 (FIG. 3) when instrument 10 is mounted on robotic surgical system 500 (FIG. 3), to enable robotic operation of actuation assembly 100 to provide the above-detailed functionality. That is, robotic surgical system 500 (FIG. 3) selectively provides rotational inputs to inputs 110-140 of actuation assembly 100 to articulate end effector assembly 40, grasp tissue between jaw members 42, 44, and/or cut tissue grasped between jaw members 42, 44. However, it is also contemplated that actuation assembly 100 be configured to interface with any other suitable surgical system, e.g., a manual surgical handle, a powered surgical handle, etc. For the purposes herein, robotic surgical system 500 (FIG. 3) is generally described.

Turning to FIG. 3, robotic surgical system 500 is configured for use in accordance with the present disclosure. Aspects and features of robotic surgical system 500 not germane to the understanding of the present disclosure are omitted to avoid obscuring the aspects and features of the present disclosure in unnecessary detail.

Robotic surgical system 500 generally includes a plurality of robot arms 502, 503; a control device 504; and an operating console 505 coupled with control device 504. Operating console 505 may include a display device 506, which may be set up in particular to display three-dimensional images; and manual input devices 507, 508, by means of which a person, e.g., a surgeon, may be able to telemanipulate robot arms 502, 503 in a first operating mode. Robotic surgical system 500 may be configured for use on a patient 513 lying on a patient table 512 to be treated in a minimally invasive manner. Robotic surgical system 500 may further include a database 514, in particular coupled to control device 504, in which are stored, for example, preoperative data from patient 513 and/or anatomical atlases.

Each of the robot arms 502, 503 may include a plurality of members, which are connected through joints, and a mounted device which may be, for example, a surgical tool "ST." One or more of the surgical tools "ST" may be instrument 10 (FIG. 1), thus providing such functionality on a robotic surgical system 500.

Robot arms 502, 503 may be driven by electric drives, e.g., motors, connected to control device 504. Control device 504, e.g., a computer, may be configured to activate the motors, in particular by means of a computer program, in such a way that robot arms 502, 503, and, thus, their mounted surgical tools "ST" execute a desired movement and/or function according to a corresponding input from manual input devices 507, 508, respectively. Control device 504 may also be configured in such a way that it regulates the movement of robot arms 502, 503 and/or of the motors.

Figure 4:
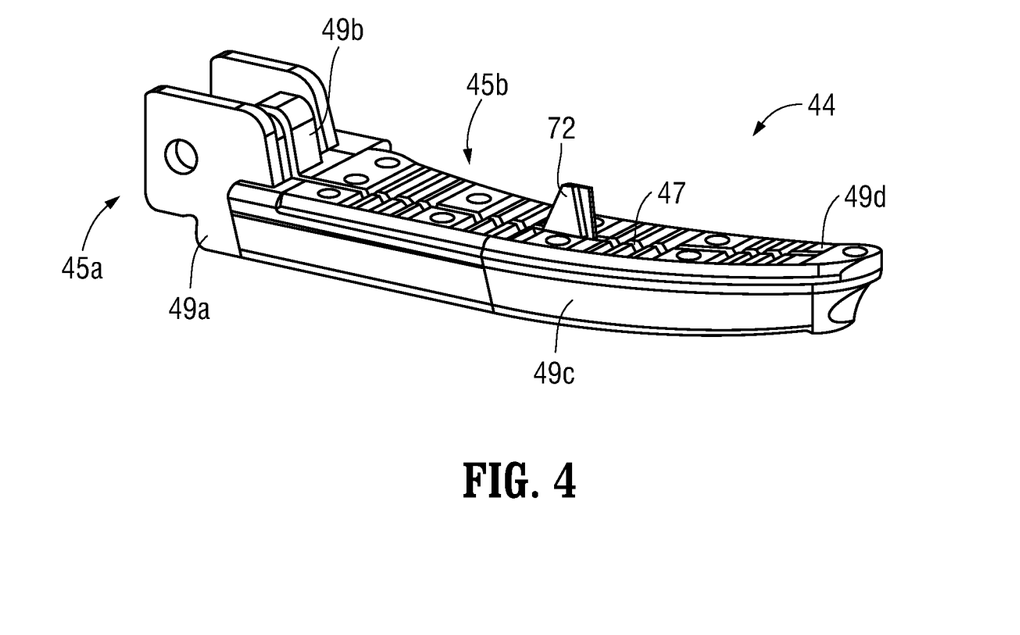
FIG. 4 is a perspective view of a jaw member of an end effector assembly of the surgical instrument of FIG. 1 including a cutting element extending therethrough.
Figure 5:
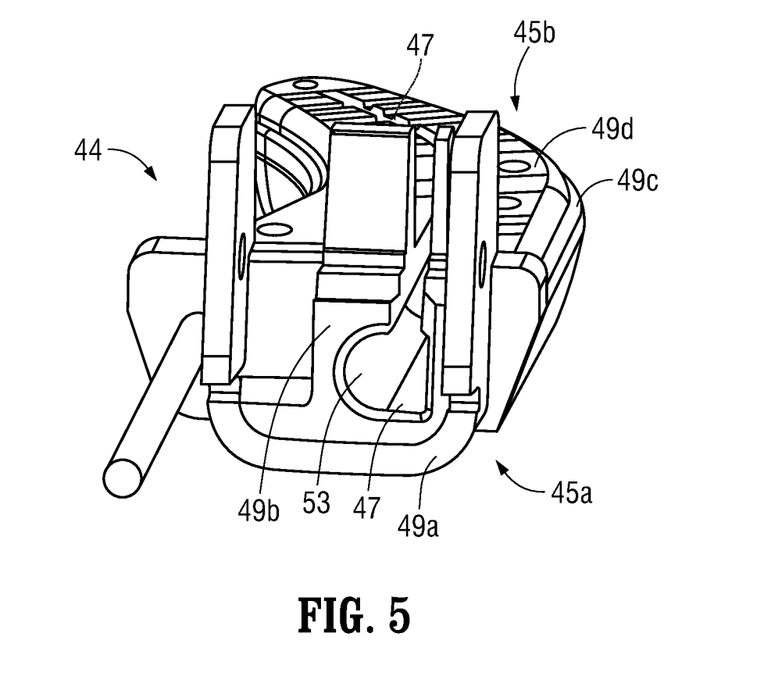
FIG. 5 is a proximal end view of the jaw member of FIG. 4.

Turning to FIGS. 4 and 5, jaw member 44 is shown. Jaw member 44, as noted above, includes proximal flange portion 45a and distal body portion 45b. Jaw member 44, more specifically, includes a structural jaw 49a, an internal spacer 49b, an outer housing 49c, and an electrically-conductive plate 49d defining tissue-contacting surface 48. Structural jaw 49a provides structural support to jaw member 44 and includes a distal portion that supports the components of distal body portion 45b of jaw member 44 thereon and a proximal portion that extends proximally from distal body portion 45b to form proximal flange portion 45a of jaw member 44. The distal portion of structural jaw 49a, together with internal spacer 49b, outer housing 49c, and electrically-conductive plate 49d, form distal body portion 45b of jaw member 44. Internal spacer 49b is disposed on the distal portion of structural jaw 49a, electrically-conductive plate 49d is disposed on internal spacer 49b, and outer housing 49c is disposed about internal spacer 49b, the distal portion of structural jaw 49a, and a portion of electrically-conductive plate 49d to secure these components to one another, e.g., via overmolding, although other configurations are also contemplated.

As noted above, jaw member 44 defines a longitudinally-extending channel 47. Channel 47 is formed by cooperating channel portions defined within electrically-conductive plate 49d and internal spacer 49b. Internal spacer 49b further includes a partially-cylindrical cut-out 53 that communicates with channel 47. Channel 47 and cut-out 53 are open at the proximal end of distal body portion 45b of jaw member 44 to permit insertion of cutting element 72 and cutting actuation rod 74 (FIG. 6) therethrough.

Figure 6:
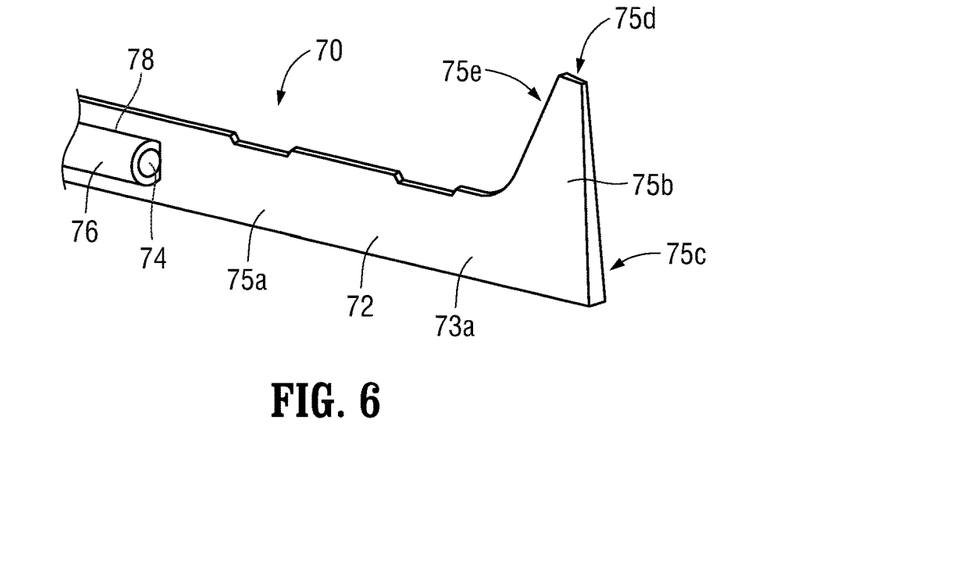
FIG. 6 is a perspective view of the cutting element of FIG. 4 including an actuation rod connected thereto.

Referring to FIG. 6, cutting assembly 70 is shown. As noted above, cutting assembly 70 includes cutting element 72 and cutting actuation rod 74. A ferrule 76 engaged about a distal end portion of cutting actuation rod 74 is secured within a slot 78 defined within a proximal portion of cutting element 72 to securely engage cutting actuation rod 74 with cutting element 72 such that actuation of cutting actuation rod 74 reciprocates cutting element 72 between jaw members 42, 44 to cut tissue grasped between tissue-contacting surfaces 46, 48 (see FIG. 1). Ferrule 76 and, thus, cutting actuation rod 74 are offset relative to cutting element 72 such that ferrule 76 and cutting actuation rod 74 protrude farther (or completely) from one side of cutting element 72 and less (or not at all) from the other side.

Cutting element 72 defines a vertically-oriented plate-like configuration wherein cutting element 72 defines relatively broad side surfaces 73a, 73b (FIGS. 7A-7B), respectively, and relatively narrow top and bottom surfaces 73c, 73d, respectively. Cutting element 72 further includes a body portion 75a defining a substantially constant height and a distal fin 75b extending distally and upwardly from body portion 75a. Distal fin 75b defines a height greater than the height of body portion 75a and includes a distal edge 75c, an upper edge 75d, and a proximal edge 75e that define the fin-shaped configuration thereof. Distal edge 75c may be angled proximally (in a bottom-to-top direction) or may define any other suitable configuration including angled, curved, or other linear or non-linear configurations. Cutting element 72 may be at least partially flexible in lateral directions, e.g., perpendicular to broad side surfaces 73a, 73b, to enable reciprocation of cutting element 72 through curved channels 47 such as, for example, in an end effector assembly wherein one or both of the jaw members defines a curved configuration (e.g., jaw member 44 (FIGS. 4 and 5)). Different configurations of cutting element 72 are described in greater detail below with reference to FIGS. 7A-11.

Figure 7A:
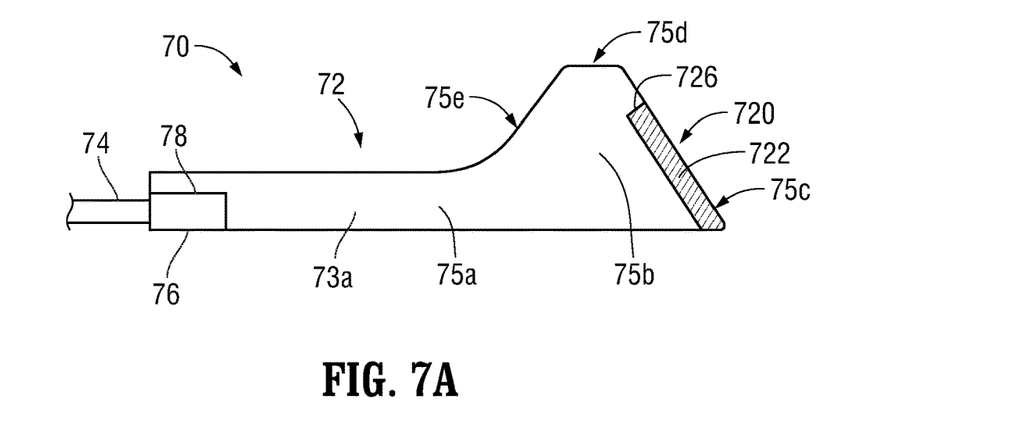
FIGS. 7A and 7B are side views of one configuration of the cutting element of FIG. 4.
Figure 7B:
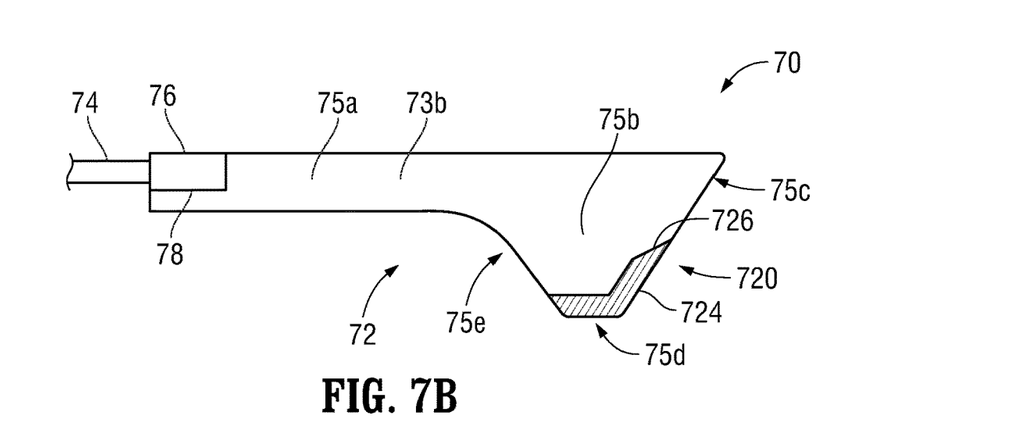
Figure 8:
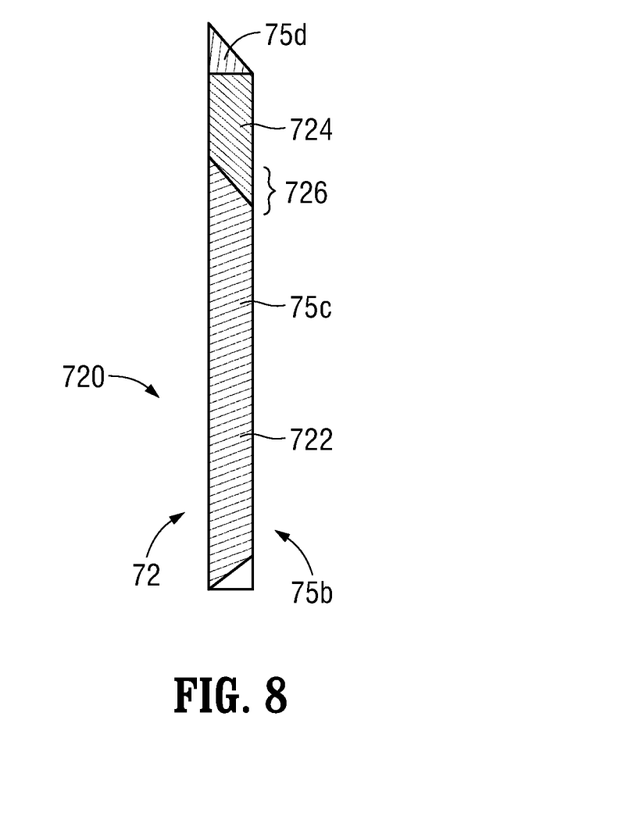
FIG. 8 is a distal end view of the cutting element configuration of FIGS. 7A and 7B.

Turning to FIGS. 7A-8, cutting element 72 may define, for example, a sharpened cutting edge 720 extending along at least a portion of distal edge 75c and/or upper edge 75d of distal fin 75b to facilitate cutting tissue upon distal advancement of cutting element 72 between jaw members 42, 44 (FIG. 1). Cutting edge 720, more specifically, is formed via first and second bevels 722, 724 defined within distal edge 75c and/or upper edge 75d. First bevel 722 is defined within distal cutting edge 75c on first broad side 73a of cutting element 72, while second bevel 722 is defined within distal edge 75c on second broad side 73b of cutting element 72. Second bevel 722 may further extend to be defined along a portion of upper edge 75d.

First bevel 722 may extend at least 50% of a length of distal edge 75c, at least 60% of the length of distal edge 75c, at least 70% of the length of distal edge 75c, or at least 80% of the length of distal edge 75c and, thus, second bevel 724 may extend at most 50% of the length of distal edge 75c, at most 40% of the length of distal edge 75c, at most 30% of the length of distal edge 75c, or at most 20% of the length of distal edge 75c, respectively.

A transition portion 726 of distal edge 75c is defined in the vicinity of where first bevel 722 ends and second bevel 724 begins. Transition portion 726 may be defined as a line wherein first bevel 722 ends and second bevel 724 begins. In configurations wherein transition portion 726 is a line, the line may be linear, curved, or including multiple different segments (curved, angled, etc.). The line may extend transversely across distal edge 75c or may be disposed at an acute angle relative thereto. Additionally or alternatively, transition portion 726 may be defined by an overlap wherein first and second bevels 722, 724 overlap one another for a portion of distal edge 75c, e.g., 15%, 10%, or 5% of the length of distal edge 75c. Further still, transition portion 726 may be defined as a gap between the end of first bevel 722 and the beginning of second bevel 724.

In any of the above configurations, transition portion 726 may be positioned such that, when cutting element 72 is disposed within channels 47 of jaw members 42, 44 (FIGS. 1 and 5), transition portion 726 is at least partially exposed between tissue-contacting surfaces 46, 48 of jaw member 42, 44, respectively (FIG. 1). Additionally or alternatively, first and second bevels 722, 724 may both be exposed between tissue-contacting surfaces 46, 48 of jaw member 42, 44, respectively (FIG. 1). Bevels 722, 724 in any of the above-detailed configurations, provide a sharpened distal edge 75c of cutting element 72 to facilitate cutting tissue grasped between jaw member 42, 44 (FIG. 1) upon distal advancement of cutting element 72 therebetween.

In some configurations, second bevel 724 further extends from distal edge 75c along at least a portion of a length of upper edge 75d of distal fin 75b, e.g., at least 50% of the length of upper edge 75d, at least 60% of the length of upper edge 75d, at least 70% of the length of upper edge 75d, or at least 80% of the length of upper edge 75d. This, at least a portion of upper edge 75d is sharpened to facilitate cutting tissue therewith upon distal advancement of cutting element 72.

Second bevel 724 may additionally extend from upper edge 75d of distal fin 75b along at least a portion of a length of proximal edge 75e thereof, e.g., at least 5% of the length of proximal edge 75e, at least 10% of the length of proximal edge 75e, or at least 20% of the length of proximal edge 75e to further facilitate cutting of tissue.

Figure 9:
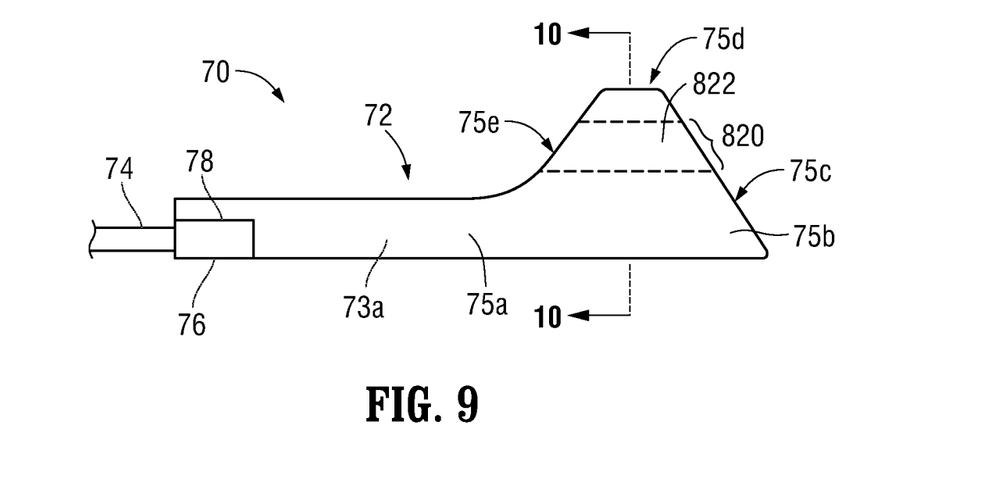
FIG. 9 is a side view of another configuration of the cutting element of FIG. 4.
Figure 10:
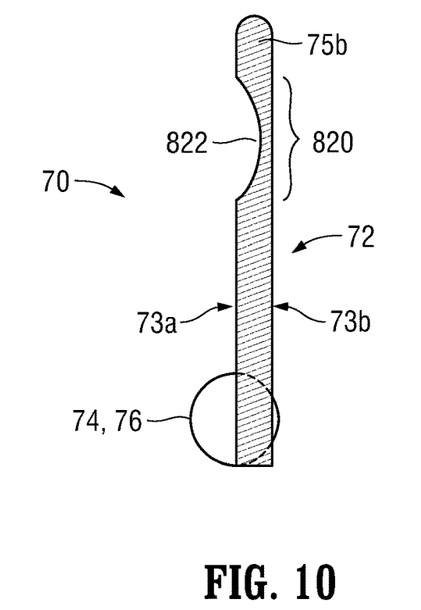
FIG. 10 is a transverse, cross-sectional view taken across section line "10-10" of FIG. 9.
Figure 11:
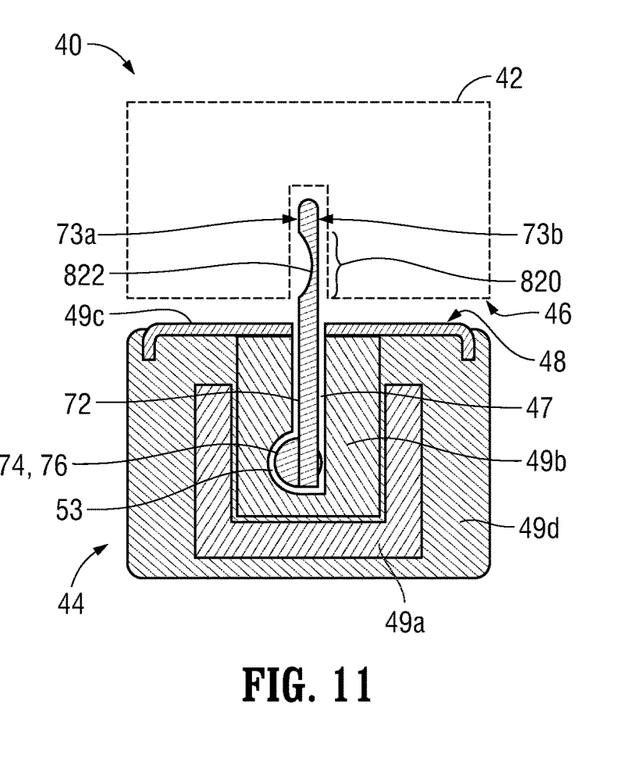
FIG. 11 is a transverse, cross-sectional view of the end effector assembly of the surgical instrument of FIG. 1 including the cutting element configuration of FIG. 9 extending therethrough.

Turning to FIGS. 9-11, cutting element 72 may include an asymmetric thinned section 820 of distal fin 75b that defines a depression 822 within one of the broad side surfaces, e.g., broad side surface 73a, of cutting element 72. Cutting element 72 may further include sharpened cutting edge 720 (FIGS. 7A and 7B) or any other suitable sharpened, dull, or other suitable mechanical, electromechanical, or electrical cutting edge defined on distal edge 75c and/or upper edge 75d.

Thinned section 820 defines a reduced thickness portion of distal fin 75b of cutting element 72 as compared to a maximum and/or average thickness of distal fin 75b of cutting element 72. The reduced width may, in aspects, be about at least 50% of the maximum and/or average thickness of distal fin 75b, at least 60% of the maximum and/or average thickness of distal fin 75b, at least 70% of the maximum and/or average thickness of distal fin 75*b*, or at least 80% of the maximum and/or average thickness of distal fin 75*b*. Thinned section 820 may extend fully across distal fin 75*b* from distal edge 75*c* to proximal edge 75*e* or may extend only a portion thereof from distal edge 75*c*, from proximal edge 75*e*, or therebetween. Thinned section 820 may extend across a portion of distal fin 75*b* that protrudes upwardly from body portion 75*a* of cutting element 72, or may extend to the portion of distal fin 75*b* that extends distally form 75*a*.

Depression 822 may define an arcuate shape in transverse cross-section, or any other suitable transverse cross-sectional configuration. Depression 822 may be positioned such that, when cutting element 72 is disposed within channels 47 of jaw members 42, 44 (FIG. 11), depression 822 is at least partially exposed between tissue-contacting surfaces 46, 48 of jaw member 42, 44, respectively. Thinned section 820, and depression 822 formed thereby, help maintain cutting element 72 in a vertical orientation and inhibit leaning of cutting element 72 such that cutting element 72 is maintained in substantially perpendicular orientation relative to tissue-contacting surfaces 46, 48 of jaw member 42, 44, respectively, as cutting element 72 is reciprocated therebetween. In configurations wherein jaw members 42, 44 and the channels 47 thereof define curved configuration and, thus, wherein cutting element 72 is reciprocated along a curved travel path, depression 822 may be formed within cutting element 72 on the convex side of the curved travel path. Additionally or alternatively, depression 822 may be formed within cutting element 72 on the same side in which ferrule 76 (and/or cutting actuation rod 74) protrudes farther (or completely) from cutting element 72. As such, this side corresponds to the side where cut-out 53 is disposed relative to channel 47.

It will be understood that various modifications may be made to the aspects and features disclosed herein. Therefore, the above description should not be construed as limiting, but merely as exemplifications of various aspects and features. Those skilled in the art will envision other modifications within the scope and spirit of the claims appended thereto.

What is claimed is:

1. An end effector assembly of a surgical instrument, comprising:
   first and second jaw members at least one of which is movable relative to the other between a spaced-apart position and an approximated position to grasp tissue between opposing tissue-contacting surfaces thereof, at least one of the first or second jaw members defining a channel; and
   a cutting element configured to reciprocate through the channel and between the first and second jaw members to cut tissue grasped between the opposing tissue-contacting surfaces, the cutting element including first and second side surfaces and a distal edge, wherein a first bevel is defined along the distal edge on the first side surface and wherein a second bevel is defined along the distal edge on the second side surface, at least a portion of the first bevel extending along a first portion of the distal edge that does not include the second bevel and at least a portion of the second bevel extending along a second portion of the distal edge that does not include the first bevel, wherein the first and second bevels are configured such that the first and second portions of the distal edge are sharpened to facilitate cutting tissue upon distal advancement of the cutting element between the first and second jaw members.

2. The end effector assembly according to claim 1, wherein the cutting element includes a proximal body and a distal fin, the distal fin defined by the distal edge, an upper edge extending from the distal edge, and a proximal edge extending from the upper edge.

3. The end effector assembly according to claim 2, wherein the second bevel extends to or along at least a portion of the upper edge.

4. The end effector assembly according to claim 1, wherein a transition is defined on the distal edge between the first bevel and the second bevel.

5. The end effector assembly according to claim 4, wherein the transition is one of: an overlapping portion of the first and second bevels; a gap between the first and second bevels; or a line defining an end of one of the first or second bevels and a beginning of the other of the first or second bevels.

6. The end effector assembly according to claim 4, wherein the transition is exposed between the first and second jaw members upon reciprocation of the cutting element therethrough.

7. The end effector assembly according to claim 1, wherein at least a portion of each of the first and second bevels is exposed between the first and second jaw members upon reciprocation of the cutting element therethrough.

8. The end effector assembly according to claim 1, further comprising a cutting actuation rod attached to the cutting element and configured to reciprocate the cutting element between the first and second jaw members.

9. The end effector assembly according to claim 8, wherein the cutting actuation rod is configured to extend through a cut-out defined within one of the first or second jaw members and disposed in communication with the channel.

10. An end effector assembly of a surgical instrument, comprising: first and second jaw members at least one of which is movable relative to the other between a spaced-apart position and an approximated position to grasp tissue between opposing tissue-contacting surfaces thereof, at least one of the first or second jaw members defining a channel; and a cutting element configured to reciprocate through the channel and between the first and second jaw members to cut tissue grasped between the opposing tissue-contacting surfaces, the cutting element including a proximal body and a distal fin defining a height greater than a height of the proximal body, the distal fin having first and second side surfaces and defined by a distal edge, an upper edge extending from the distal edge, and a proximal edge extending from the upper edge, wherein the distal fin defines a first thickness transversely between the first and second side surfaces and includes a thinned portion defining a depression within the first side surface thereof, wherein the depression extends from the proximal edge to the distal edge of the distal fin; the distal fin defining a second thickness transversely between the depression and the second side surface that is less than the first thickness.

11. The end effector assembly according to claim 10, wherein at least a portion of the distal edge is sharpened to facilitate cutting tissue upon distal advancement of the cutting element between the first and second jaw members.

12. The end effector assembly according to claim 10, wherein the thinned portion is defined within a section of the distal fin that extends upwardly beyond the height of the proximal body.

13. The end effector assembly according to claim 10, wherein the thinned portion extends across the distal fin from the distal edge to the proximal edge.

14. The end effector assembly according to claim 10, further comprising a cutting actuation rod attached to the proximal body of the cutting element and configured to reciprocate the cutting element between the first and second jaw members.

15. The end effector assembly according to claim 14, wherein the cutting actuation rod is configured to extend through a cut-out defined within one of the first or second jaw members and disposed in communication with the channel.

16. The end effector assembly according to claim 10, wherein the at least one channel is curved such that the cutting element defines a curved cutting path when reciprocated through the channel.

17. The end effector assembly according to claim 16, wherein the depression defined within the first side surface of the cutting element is disposed on a convex side of the curved cutting path.

18. The end effector assembly according to claim 16, wherein the first and second jaw members are curved and wherein the at least one channel is curved similarly as the first and second jaw members.

* * * * *